(12) United States Patent
Ward et al.

(10) Patent No.: US 8,394,106 B2
(45) Date of Patent: Mar. 12, 2013

(54) CEMENT SHROUD FOR USE WITH CEMENTED PROSTHETIC IMPLANT

(75) Inventors: Ryan T. Ward, Columbia City, IN (US); Mark A. Wise, Warsaw, IN (US)

(73) Assignee: Zimmer, Inc., Warsaw, IN (US)

( * ) Notice: Subject to any disclaimer, the term of this patent is extended or adjusted under 35 U.S.C. 154(b) by 0 days.

(21) Appl. No.: 13/433,977

(22) Filed: Mar. 29, 2012

(65) Prior Publication Data

US 2012/0191212 A1 Jul. 26, 2012

Related U.S. Application Data

(63) Continuation of application No. 12/106,508, filed on Apr. 21, 2008, now Pat. No. 8,172,851.

(51) Int. Cl.
*A61B 17/56* (2006.01)
*A61F 2/32* (2006.01)

(52) U.S. Cl. ............. 606/92; 623/22.12; 623/22.28

(58) Field of Classification Search ............ 606/92; 623/22.12, 22.28

See application file for complete search history.

(56) References Cited

U.S. PATENT DOCUMENTS

| | | | |
|---|---|---|---|
| 4,327,449 A | 5/1982 | Charnley | |
| 4,466,435 A | 8/1984 | Murray | |
| 4,627,434 A | 12/1986 | Murray | |
| 4,711,233 A | 12/1987 | Brown | |
| 4,815,454 A | 3/1989 | Dozier, Jr. | |
| 5,062,853 A | 11/1991 | Forte | |
| 5,092,891 A | 3/1992 | Kummer et al. | |
| 5,507,748 A | 4/1996 | Sheehan et al. | |
| 5,800,439 A | 9/1998 | Clyburn | |
| 5,824,108 A | 10/1998 | Huebner | |
| 5,849,014 A | 12/1998 | Mastrorio et al. | |
| 6,019,766 A | 2/2000 | Ling et al. | |
| 6,110,179 A | 8/2000 | Flivik et al. | |
| 6,264,698 B1 * | 7/2001 | Lawes et al. | 623/22.12 |
| 6,592,589 B2 | 7/2003 | Hajianpour | |
| 2002/0177854 A1 | 11/2002 | Tuke et al. | |
| 2003/0050703 A1 | 3/2003 | Harris et al. | |
| 2004/0015238 A1 | 1/2004 | Buehler et al. | |
| 2004/0225369 A1 | 11/2004 | Lakin et al. | |
| 2005/0080490 A1 | 4/2005 | Bertram, III | |
| 2005/0203537 A1 | 9/2005 | Wiley | |
| 2006/0058885 A1 | 3/2006 | Wozencroft | |

OTHER PUBLICATIONS

Surgical Technique—Zimmer Trabecular Metal Revision Shell, 97-7255-008-00 Rev. 2 5ML, 2002, 2006.
Brochure—Zimmer Trabecular Metal Acetabular Revision System, 97-7255-049-00 5ML, 2007.
Zimmer, "Allen Medullary Bone Plug Kit" Features of the Allen Medullary Bone Plug Kit and Ordering Information. No. 97-8011-05 Rev. 1 5MZ printed in USA 1999, 2000, Zimmer, Inc., 1 page.
The Zimmer Complete Bone Cement System, Product Brochure, Zimmer, Inc., available on or before Apr. 20, 2008.

* cited by examiner

*Primary Examiner* — Bruce E Snow
*Assistant Examiner* — Melissa Hoban
(74) *Attorney, Agent, or Firm* — Schwegman, Lundberg & Woessner

(57) ABSTRACT

A shroud for protecting exterior portions of a prosthetic implant from adhesive and a method for utilizing the same. The shroud includes a hub, a rim, and at least one bridge connecting the hub and the rim. The rim of the shroud may be sized to cover substantially the same area as a guard of the implant. The method of utilizing the shroud involves securing the shroud to the prosthetic implant. A quantity of adhesive is provided, and the prosthetic implant is secured thereto. The shroud is removed from the implant, and then the guard is secured to the implant.

13 Claims, 8 Drawing Sheets

CEMENT SHROUD FOR USE WITH CEMENTED PROSTHETIC IMPLANT

CROSS REFERENCE TO RELATED APPLICATION

The present application is a continuation of U.S. patent application Ser. No. 12/106,508, now U.S. Pat. No. 8,172,851, filed Apr. 21, 2008, the disclosure of which is hereby expressly incorporated by reference herein in its entirety.

BACKGROUND

1. Field of the Invention

The present invention relates to cemented prosthetic implants. More particularly, the present invention relates to a device for shrouding or protecting prosthetic implants from adhesive, and to a method for utilizing the same.

2. Description of the Related Art

Joint arthroplasty is a surgical procedure for replacing damaged components of a joint with prosthetic components. Such damage may be caused by, for example, traumatic injury or some form of arthritis, such as osteoarthritis. Joint arthroplasty may relieve pain and restore motion in the damaged joint.

The hip joint, in particular, is a ball-and-socket joint between the head of the femur (ball) and the acetabulum of the pelvis (socket). Therefore, arthroplasty of the hip joint can involve replacing the femoral head and/or the acetabulum with prosthetic implants. A prosthetic acetabulum can include a liner that receives and interacts with the prosthetic femoral head. This liner may be secured to an outer acetabular shell or directly to the pelvis. In some cases, the liner is secured in place using adhesive, such as bone cement.

The present invention involves the use of bone cement to secure a liner in place. As the liner is pushed against the acetabular shell or the pelvis, excess bone cement seeps out around the liner and onto exterior portions of the liner. To avoid disturbing the drying cement between the components, a surgeon may be forced to allow this excess bone cement to dry and harden onto exterior portions of the components, including a rim of the liner. Once the liner is secured in place, the hardened excess bone cement must be cleared away as much as possible from the rim of the liner using a standard surgical tool, such as a curette or a scraper. The step of clearing away the excess cement becomes especially important when the prosthetic implant requires attachment of an additional component, such as a guard, atop the rim of the liner.

SUMMARY

The present invention relates to a shroud for protecting exterior portions of a prosthetic implant from adhesive. The prosthetic implant includes a liner having a rim. The liner is configured to be implanted into a patient's body using adhesive and is configured to receive an opposing articular component.

According to an embodiment of the present invention, a prosthetic device is provided including a liner, a guard, and a shroud. The liner is configured to be implanted into a patient's body using adhesive and is configured to receive an opposing articular component, said liner including a rim. The guard is designed to attach to the liner to secure the opposing articular component within the liner. The shroud includes a rim and a hub, said rim sized to cover substantially the same area of the liner as the guard when the guard is secured to the liner, said hub having a concave impaction surface that is configured to receive a convex impaction tool to force the liner into the adhesive.

According to another embodiment of the present invention, a prosthetic device is provided having a first, shrouded configuration and a second, constrained configuration. The device includes a liner, a guard, and a shroud. The liner includes a mating surface that is configured to receive adhesive, an articulating surface that is configured to receive an opposing articular component, a rim, and at least one constraining extension that extends from the rim, the at least one constraining extension having an inner side and an outer side. The shroud couples to the liner in the first, shrouded configuration to shield the liner from adhesive, the inner side of the at least one constraining extension frictionally engaging the shroud in the first, shrouded configuration to couple the shroud to the liner. The guard couples to the liner in the second, constrained configuration, the guard frictionally engaging the outer side of the at least one constraining extension in the second, constrained configuration to capture the opposing articular component in the liner.

The present invention also relates to a method for protecting exterior portions of the prosthetic implant from adhesive. The method involves providing a shroud and a guard and securing the shroud to the prosthetic implant. A quantity of adhesive is provided, and the prosthetic implant is secured thereto. The shroud is removed from the implant, and then the guard is secured to the implant.

Advantageously, the present invention prevents excess adhesive from seeping out around the liner and onto exterior portions of the implant. Also, the present invention prevents a surgeon from having to clear away the excess adhesive before attaching an additional component, such as a guard, atop the rim of the liner.

BRIEF DESCRIPTION OF THE DRAWINGS

The above-mentioned and other features and advantages of this invention, and the manner of attaining them, will become more apparent and the invention itself will be better understood by reference to the following description of embodiments of the invention taken in conjunction with the accompanying drawings, wherein.

Corresponding reference characters indicate corresponding parts throughout the several views. The exemplifications set out herein illustrate exemplary embodiments of the inven-

DETAILED DESCRIPTION

Figure 1:
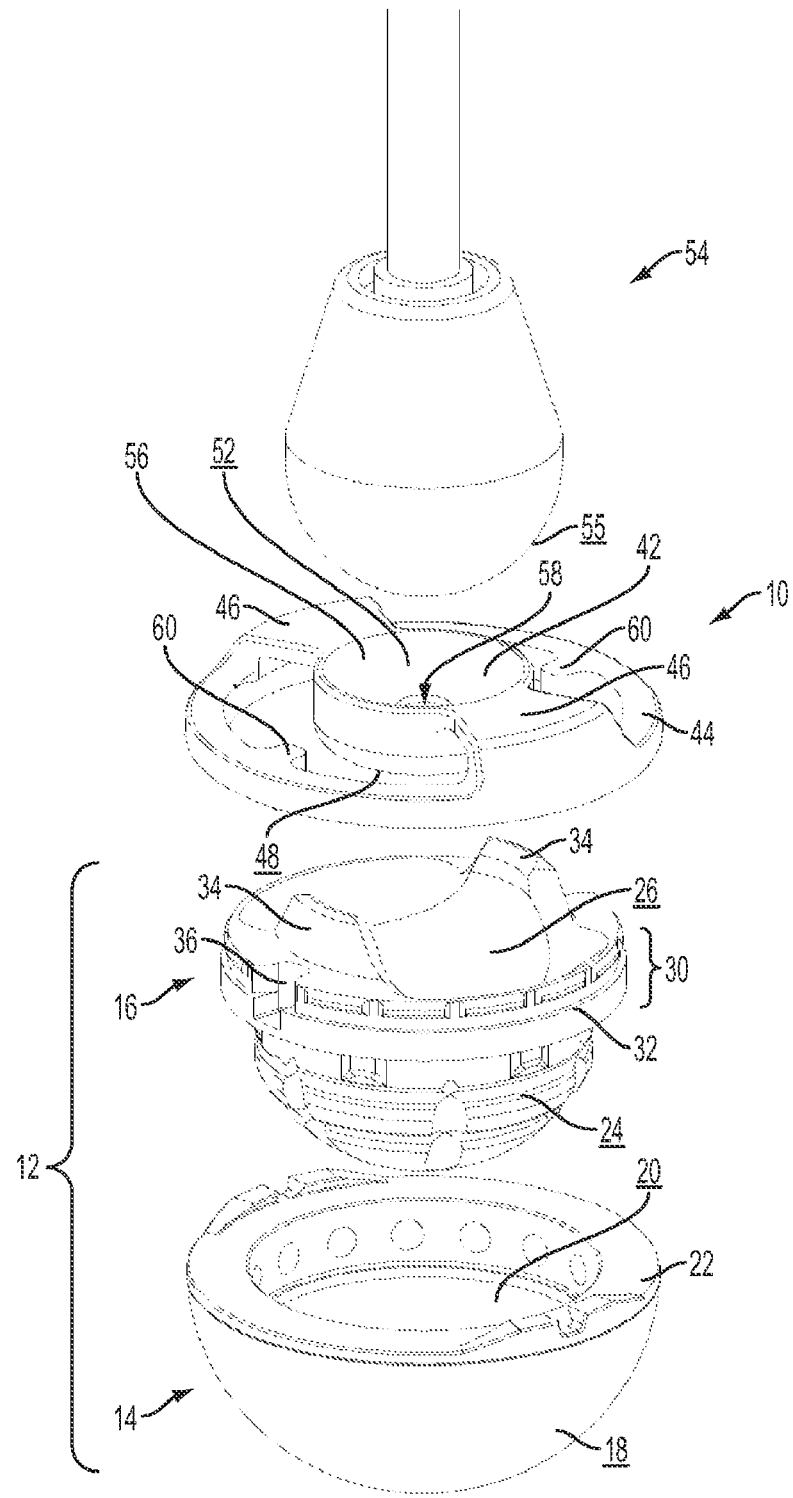
FIG. 1 is a perspective, exploded view of an impaction tool, a shroud, a liner, and an acetabular shell of the present invention.
Figure 2:
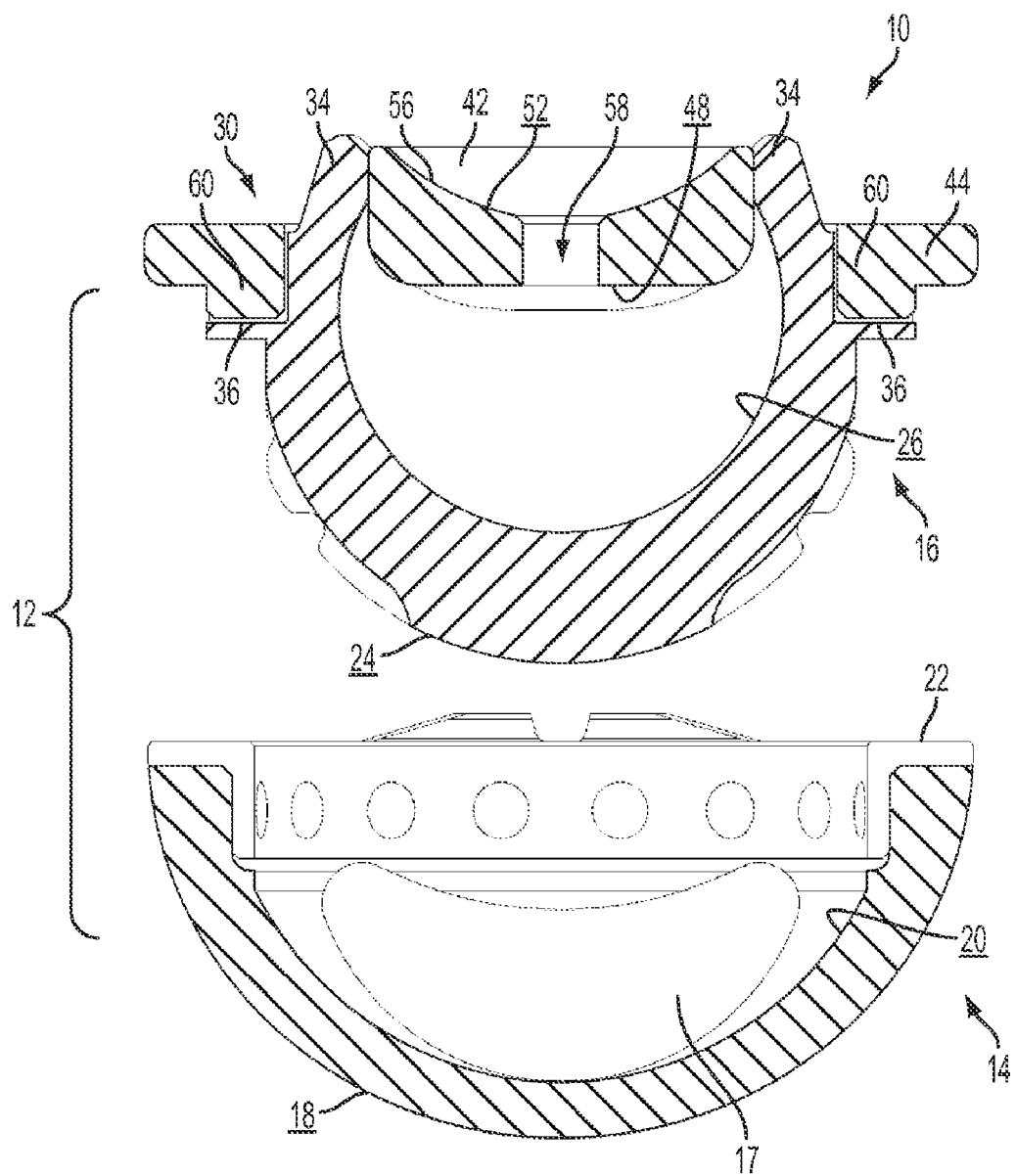
FIG. 2 is a cross-sectional view of a shroud, a liner, and an acetabular shell of the present invention before the liner is positioned within the acetabular shell.
Figure 3:
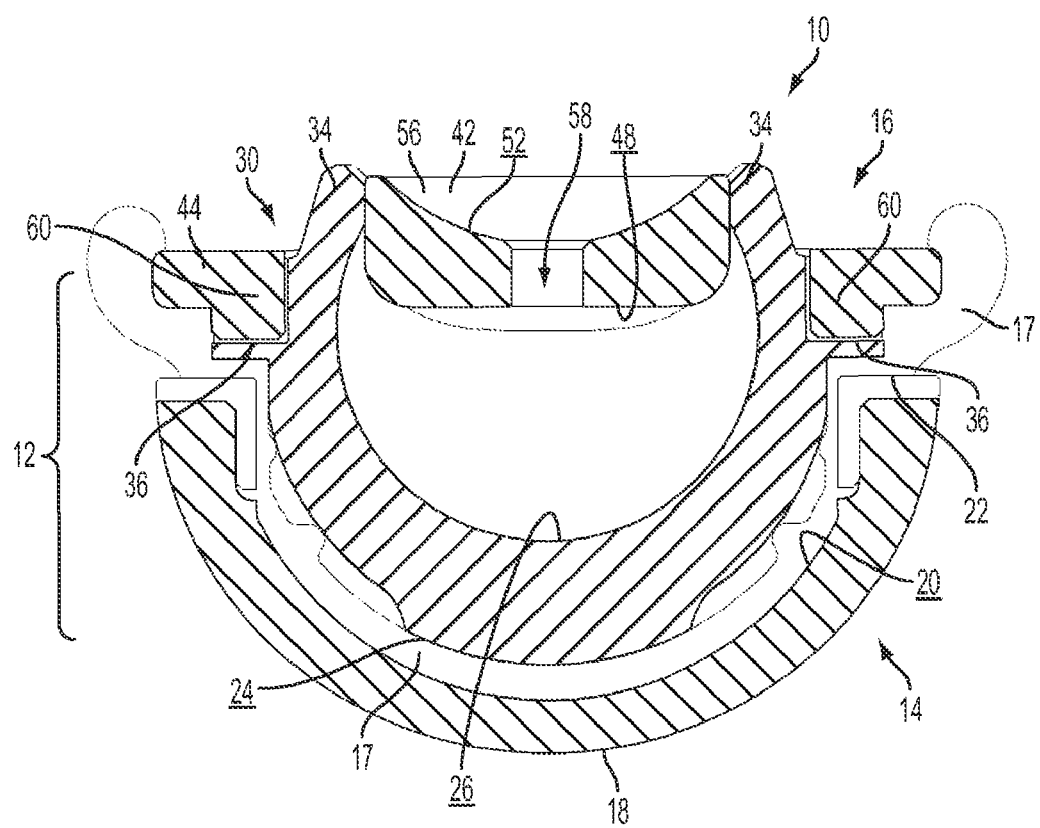
FIG. 3 is a cross-sectional view of the shroud, the liner, and the acetabular shell of FIG. 2 after the liner is positioned within the acetabular shell.

As shown in FIGS. 1-3, shroud 10 is provided along with implant 12. As illustrated, implant 12 is in the form of a prosthetic acetabulum. While implant 12 is described and depicted herein as being designed for attachment to the pelvis during hip arthroplasty, implant 12 of the present invention may be secured in other locations in accordance with the teachings herein. For example, implant 12 may be designed for use during shoulder arthroplasty. Implant 12 may include acetabular shell 14 and liner 16.

Referring still to FIGS. 1-3, acetabular shell 14 includes bone-contacting surface 18, mating surface 20, and rim 22 extending between bone-contacting surface 18 and mating surface 20. Bone-contacting surface 18 of acetabular shell 14 is designed for attachment to bone, such as the pelvis. Mating surface 20 of acetabular shell 14 is designed to receive and engage liner 16. In an exemplary embodiment of the present invention, both bone-contacting surface 18 and mating surface 20 of acetabular shell 14 are porous in order to promote fixation between acetabular shell 14 and the bone and between acetabular shell 14 and liner 16. In another exemplary embodiment of the present invention, bone-contacting surface 18 of acetabular shell 14 is convex to securely attach to the pelvis.

Referring still to FIGS. 1-3, liner 16 includes mating surface 24, articulating surface 26, and rim 30 extending between mating surface 24 and articulating surface 26. In an embodiment of the present invention, mating surface 24 of liner 16 is designed to engage acetabular shell 14. More specifically, mating surface 24 of liner 16 is designed to engage mating surface 20 of acetabular shell 14. In another embodiment of the present invention, mating surface 24 of liner 16 is designed for direct attachment to bone, such as the pelvis. According to this second embodiment, implant 12 need not include acetabular shell 14, as liner 16 may be secured directly to bone. Articulating surface 26 of liner 16 is designed to receive and articulate with an opposing articular component. In an exemplary embodiment of the present invention, articulating surface 26 of liner 16 is concave to receive prosthetic femoral head 28 (FIG. 5), while mating surface 24 of liner 16 is convex to fit within acetabular shell 14 or the pelvis. Liner 16 may be secured to acetabular shell 14 or to the pelvis using adhesive 17, such as bone cement.

Referring to FIGS. 1-5, rim 30 of liner 16 may include flange 32 extending around rim 30, any number of constraining extensions 34, and any number of slots 36. Constraining extensions 34 extend from rim 30 of liner 16 to provide articulating surface 26 of liner 16 with more surface area for interaction with an opposing articular component, such as prosthetic femoral head 28. Specifically, constraining extensions 34 may extend articulating surface 26 of liner 16 beyond a hemisphere to constrain prosthetic femoral head 28 from removal from liner 16. Constraining extensions 34 may be flexible to allow insertion of prosthetic femoral head 28 into liner 16 and, if necessary, to allow removal of prosthetic femoral head 28 from liner 16. Slots 36 extend into rim 30 of liner 16. Slots 36 may be designed to receive a portion of guard 38 (FIGS. 4-5), as will be described below.

Figure 4:
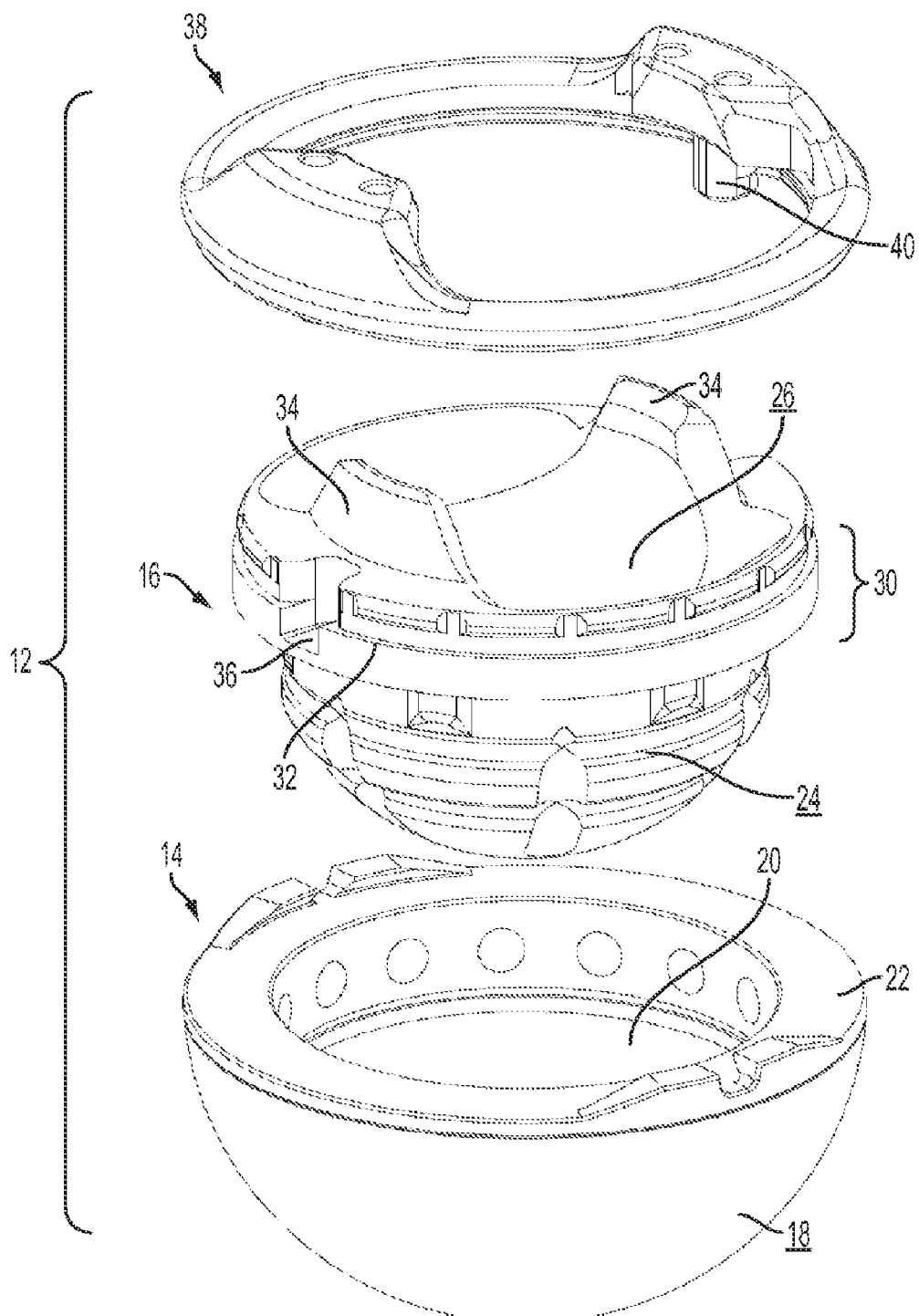
FIG. 4 is a perspective, exploded view of a liner, an acetabular shell, and a guard of the present invention.
Figure 5:
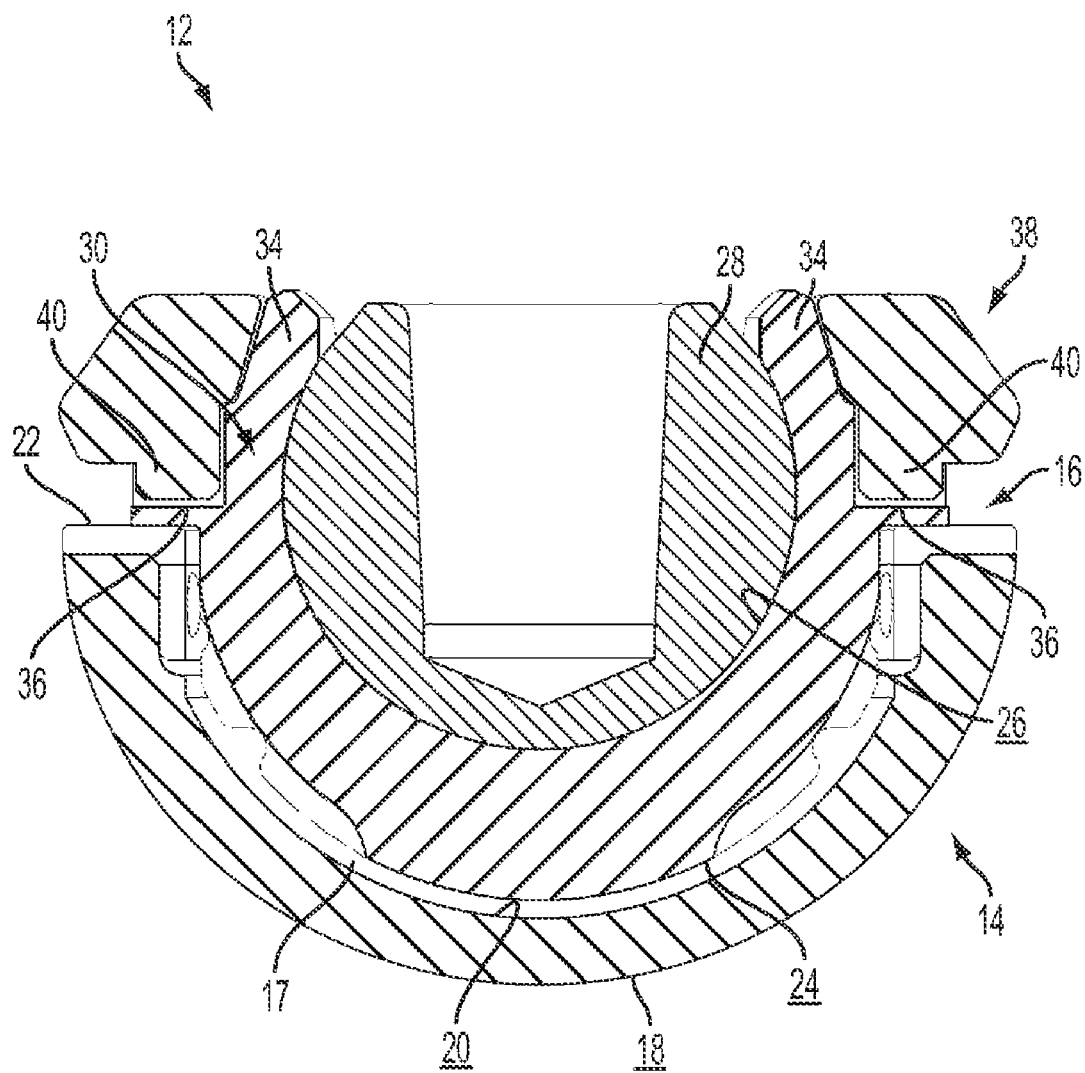
FIG. 5 is a cross-sectional view of a liner, an acetabular shell, and a guard of the present invention assembled to receive a femoral head.

Referring to FIGS. 4-5, in addition to acetabular shell 14 and liner 16, implant 12 further includes guard 38. Guard 38 may be provided to support constraining extensions 34 of liner 16 after an opposing articular component is placed within liner 16. In an exemplary embodiment, guard 38 is secured atop rim 30 of liner 16, and more specifically atop flange 32 of rim 30 of liner 16, after prosthetic femoral head 28 is placed within liner 16. Guard 38 may have a matte-type finish produced by a glass bead dry blast operation. Guard 38 includes posts 40 that extend beyond the base of guard 38 to aid in the attachment between guard 38 and liner 16 and to prevent guard 38 from rotating. Posts 40 of guard 38 are placed within slots 36 of liner 16. Guard 38 and liner 16 are designed with a tight interference fit to prevent guard 38 from separating from liner 16 in vivo. In operation, guard 38 prevents constraining extensions 34 from flexing outwardly and, therefore, prevents prosthetic femoral head 28 from withdrawing from liner 16.

Figure 6:
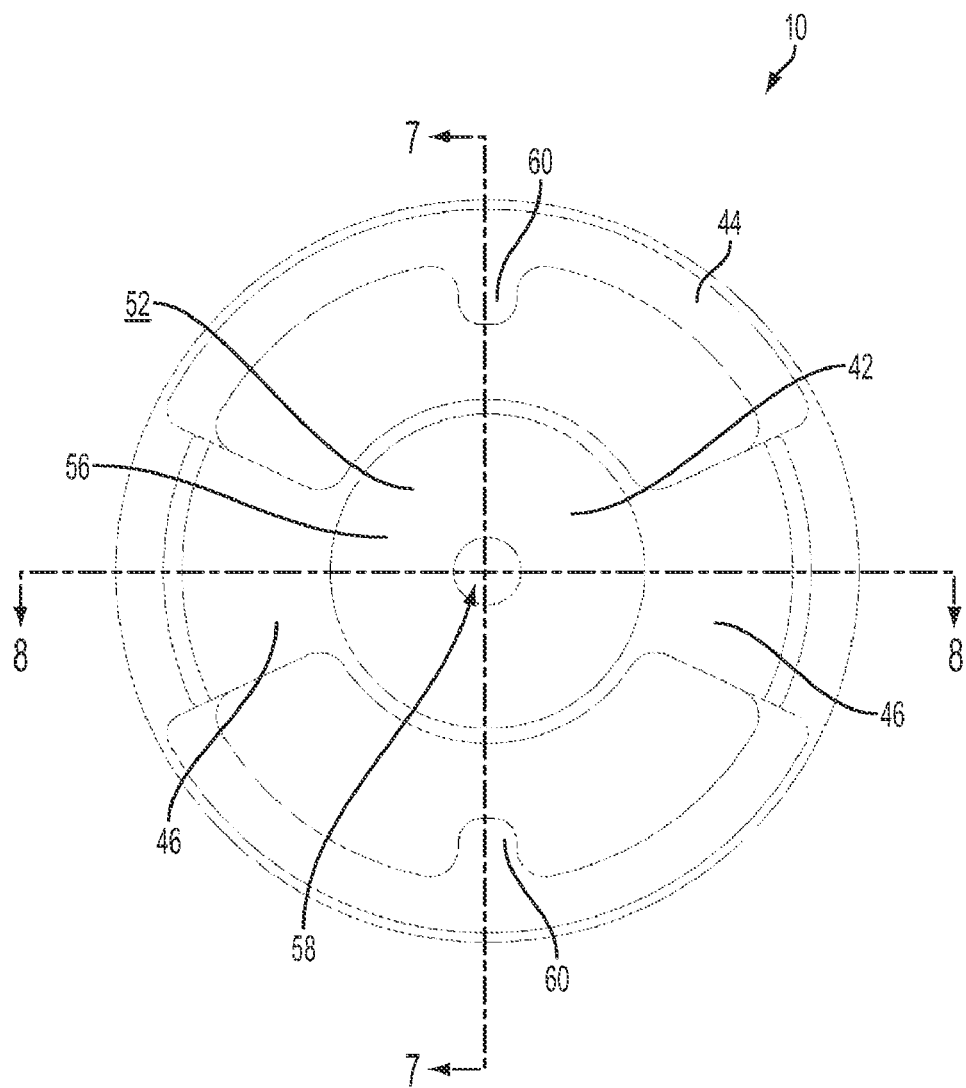
FIG. 6 is a top plan view of a shroud of the present invention.
Figure 7:
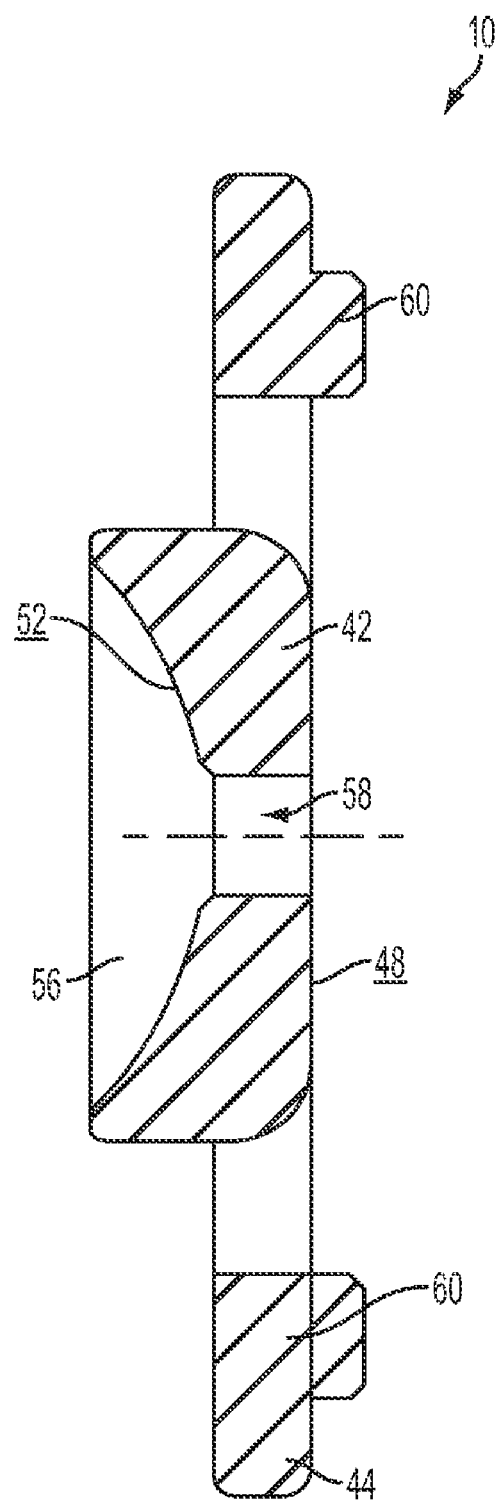
FIG. 7 is a cross-sectional view of the shroud of FIG. 6 taken along line 7-7 of FIG. 6.
Figure 8:
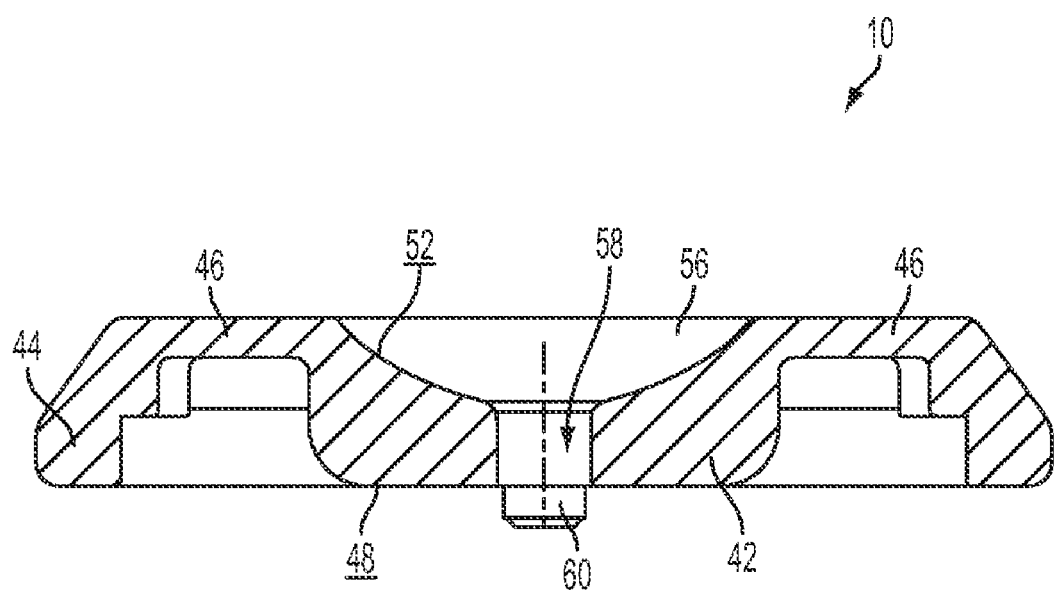
FIG. 8 is a cross-sectional view of the shroud of FIG. 6 taken along line 8-8 of FIG. 6.

Referring to FIGS. 6-8, shroud 10 is provided to protect exterior portions of implant 12 from adhesive 17 (FIGS. 2-3). Shroud 10 is a rigid device of predetermined size, and includes hub 42, rim 44, and bridge 46 connecting hub 42 and rim 44. Shroud 10 may be constructed of metal, such as 17-4 stainless steel. In an exemplary embodiment of the present invention, shroud 10 is highly polished to minimize attachment of adhesive 17 to shroud 10. Shroud 10 may be polished using any process, such as electropolishing, capable of producing a smooth enough finish to sufficiently minimize the attachment between adhesive 17, such as bone cement, and shroud 10.

Referring to FIGS. 1-3 and 6-8, hub 42 of shroud 10 includes engaging surface 48. Engaging surface 48 of shroud 10 may be sized to accommodate liner 16. More specifically, engaging surface 48 of shroud 10 may be sized to accommodate articulating surface 26 of liner 16. For example, as shown in FIG. 2, hub 42 is sized such that engaging surface 48 of hub 42 frictionally engages constraining extensions 34 of liner 16. As another example, illustrated in FIG. 2, when hub 42 of shroud 10 is received within liner 16, engaging surface 48 of hub 42 extends downward and contacts a portion of articulating surface 26 of liner 16. It is within the scope of the present invention that engaging surface 48 of hub 42 could fully engage articulating surface 26 of liner 16.

Referring still to FIGS. 1-3 and 6-8, hub 42 of shroud 10 further includes impacting surface 52 positioned substantially opposite engaging surface 48. Impacting surface 52 of shroud 10 may be sized to accommodate impaction tool 54. In an exemplary embodiment of the present invention, impaction tool 54 is the same instrument normally used to secure liner 16 to acetabular shell 14 or to the pelvis. Therefore, impacting surface 52 of shroud 10 may mimic the dimensions and contour of articulating surface 26 of liner 16 so that a standard impaction tool 54 may be used. In another exemplary embodiment of the present invention, impacting surface 52 of shroud 10 includes depression 56 that mimics the concave shape of articulating surface 26 of liner 16. Depression 56 may essentially cover impacting surface 52 of shroud 10 to form a concave surface. In this form, a standard impaction tool 54, such as a ball pusher having a rounded exterior surface 55, may be placed against impacting surface 52 of shroud 10, just as it would have been placed against articulating surface 26 of liner 16.

Referring still to FIGS. 1-3 and 6-8, hub 42 of shroud 10 includes aperture 58. More specifically, aperture 58 extends from engaging surface 48 to impacting surface 52 of hub 42. Aperture 58 may aid in removal of shroud 10 from implant 12 by providing a location to grip with a hand or a surgical tool, such as forceps.

Referring still to FIGS. 1-3 and 6-8, shroud 10 further includes rim 44 surrounding hub 42. The primary purpose of rim 44 is to shroud exterior portions of implant 12 from adhesive 17 as liner 16 is secured into acetabular shell 14 or into the pelvis. Rim 44 of shroud 10 should be sized to cover at least those portions of implant 12 as will guard 38. According to an exemplary embodiment of the present invention, rim 44 of shroud 10 should be sized to cover at least a portion of rim 30 of liner 16. According to another exemplary embodiment of the present invention, rim 44 of shroud 10 should be sized to cover flange 32 of rim 30 of liner 16.

Referring still to FIGS. 1-3 and 6-8, rim 44 of shroud 10 may include any number of projections 60. Projections 60 of shroud 10 mimic posts 40 of guard 38. Like posts 40, projections 60 are designed to fit within slots 36 of liner 16, thereby shielding slots 36 from adhesive 17. Therefore, projections 60 further assist rim 44 of shroud 10 in shielding from adhesive 17 those areas of implant 12, such as slots 36, that will later engage guard 38. Projections 60 should be sized to provide sufficient clearance for constraining extensions 34 of liner 16, as shown in FIG. 2. Projections 60 may also serve the purpose of abutting liner 16 to help secure shroud 10 to liner 16. For example, projections 60 of rim 44 may abut constraining extensions 34 of liner 16.

Referring still to FIGS. 1-3 and 6-8, shroud 10 further includes bridge 46. Bridge 46 connects hub 42 of shroud 10 to rim 44 of shroud 10. In one form thereof, bridge 46 may be continuous, extending entirely between hub 42 and rim 44. In another form thereof, illustrated in FIGS. 1 and 2, shroud 10 may include multiple bridges 46 spaced apart radially around hub 42. This embodiment may accommodate liner 16 that includes constraining extensions 34 extending from rim 30. Additionally, this embodiment may provide locations to grip with a hand or a surgical tool, such as forceps, when removing shroud 10 from liner 16.

As shown in FIGS. 1-3, a method is provided for using shroud 10 to protect exterior portions of implant 12 from adhesive 17. A first step of the present method involves attaching shroud 10 to liner 16, more specifically to rim 30 of liner 16, and even more specifically to flange 32 of rim 30 of liner 16. In one form of the present method, shroud 10 may come pre-attached to liner 16. In another form of the present method, shroud 10 may be attached to liner 16 by pressing both components together. For example, as shown in FIG. 2, shroud 10 and liner 16 may be pressed together such that constraining extensions 34 of liner 16 are frictionally engaged with hub 42 of shroud 10.

Referring to FIG. 2, another step of the present method involves applying adequate adhesive 17 to secure liner 16 in place. Adhesive 17 may be any substance capable of permanently securing liner 16 in place including, but not limited to, bone cement. In an embodiment of the present invention, illustrated in FIG. 2, adhesive 17 is applied between acetabular shell 14 and liner 16 to secure liner 16 to acetabular shell 14. In another embodiment of the present invention, adhesive 17 is applied between liner 16 and the pelvis to secure liner 16 to the pelvis without the use of acetabular shell 14.

Referring to FIG. 3, another step of the present method involves implanting liner 16 into the body while shrouding liner 16 from adhesive 17. As mentioned above, liner 16 may be attached directly to the pelvis, or liner 16 may be attached to acetabular shell 14, which contains adhesive 17 and which has already been implanted into the body. In an exemplary embodiment of the present invention, shroud 10 shall be attached to liner 16 while implanting liner 16 into the body such that shroud 10 covers at least the same portion of liner 16 as will guard 38 (FIGS. 4-5).

Referring to FIGS. 1-3, another step of the present method involves applying pressure with impaction tool 54 to shroud 10, causing liner 16 to be securely implanted into the body. More specifically, this step may involve applying pressure with impaction tool 54 to hub 42 of shroud 10. Even more specifically, this step may involve applying pressure with impaction tool 54 to impacting surface 52 of hub 42 of shroud 10. As liner 16 is pressed into the pelvis or acetabular shell 14, adhesive 17 will be forced to spread out and surround liner 16. In an exemplary embodiment, a sufficient quantity of adhesive 17 will be used to completely cover mating surface 24 of liner 16. As liner 16 is pressed further into the pelvis or acetabular shell 14, excess adhesive 17 and air may be forced to escape from between the two components. With shroud 10 in place atop liner 16, excess adhesive 17 will be prevented from traveling onto those areas occupied by shroud 10. Because shroud 10 covers at least those areas of liner 16 that will later engage guard 38, excess adhesive 17 will be prevented from traveling onto those areas of liner 16 that will later engage guard 38.

According to an exemplary embodiment of the present method, impaction tool 54 may be the same surgical tool that would have been used without shroud 10 to apply pressure directly to liner 16. This exemplary embodiment may be achieved by providing impacting surface 52 of shroud 10 that mimics articulating surface 26 of liner 16.

According to another exemplary embodiment of the present method, shroud 10 is not rigidly connected to impaction tool 54 when applying pressure with impaction tool 54 to shroud 10. If shroud 10 were to be rigidly connected to impaction tool 54, any unintended movement of impaction tool 54 could cause movement of shroud 10, which could in turn cause movement of liner 16. Such movement of liner 16, especially while adhesive 17 is curing, may cause voids or cracks to form within adhesive 17.

Referring still to FIGS. 1-3, yet another step of the present method involves removing shroud 10 from liner 16 once adhesive 17 has substantially hardened. This step may be completed using one's own hands or with a surgical tool, such as forceps. As described above, aperture 58 in shroud 10 and bridge 46 of shroud 10 are examples of some components of shroud 10 that may be gripped in order to perform this removal step. Because shroud 10 is frictionally, and not rigidly, secured to liner 16, the removal step should also avoid significant movement of liner 16 in adhesive 17.

Referring to FIG. 5, yet another step of the present method involves positioning implant 12 to engage an opposing articular component, which may be another prosthetic implant. In an exemplary embodiment of the present method, in which implant 12 forms a prosthetic acetabulum, implant 12 is positioned to receive prosthetic femoral head 28. More specifically, prosthetic femoral head 28 is inserted into liner 16 of implant 12 so that it engages articulating surface 26 of liner 16.

Referring to FIGS. 4-5, still yet another step of the present method involves attaching guard 38 to liner 16. Guard 38 may include posts 40 to aid in the attachment between guard 38 and liner 16. More specifically, posts 40 of guard 38 may be placed within slots 36 of liner 16. Guard 38 may provide support to liner 16, especially constraining extensions 34 of liner 16. In an exemplary embodiment of the present method, guard 38 is attached atop rim 30 of liner 16, and more specifically atop flange 32 of rim 30 of liner 16, after the opposing articular component, such as prosthetic femoral head 28, is inserted into liner 16. Guard 38 and liner 16 are designed with a tight interference fit to prevent guard 38 from separating from liner 16 in vivo.

A final step of the present method involves either reusing or disposing of shroud 10. In an exemplary embodiment of the present method, shroud 10 may be constructed of metal in order to minimize attachment of adhesive 17 to shroud 10. In another exemplary embodiment of the present method, shroud 10 may be constructed of a highly polished metal in order to further minimize attachment of adhesive 17 to shroud 10. By minimizing attachment of adhesive 17 to shroud 10, shroud 10 may be reused simply by sterilizing shroud 10, without having to scrape hardened adhesive 17 away from shroud 10. Rather than re-using shroud 10, it may instead be disposed of so that no cleaning away of adhesive 17 or sterilizing is required.

While this invention has been described as having preferred designs, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A prosthetic device comprising:
   a liner having an articulating surface and a liner rim;
   a guard configured to secure an opposing articular component within the liner; and
   a shroud comprising a shroud rim, a hub, and at least one bridge member, the shroud rim defining an opening and the at least one bridge member extending between the shroud rim and the hub, the at least one bridge member configured to suspend the hub within the shroud opening.

2. The device of claim 1, wherein:
   the liner rim comprises a flange; and
   the shroud rim is configured to cover the flange.

3. The device of claim 1, wherein:
   the guard comprises at least one post;
   the liner rim comprises at least one slot sized to receive the at least one post; and
   the shroud rim comprises at least one projection configured to cover the at least one slot.

4. The device of claim 1, wherein the liner further comprises at least one constraining extension extending beyond the liner rim, the at least one constraining extension configured to extend the articulating surface beyond the liner rim.

5. The device of claim 4, wherein the hub frictionally engages the at least one constraining extension when the shroud is secured to the liner.

6. The device of claim 1, wherein the hub includes a concave impacting surface configured to receive a convex impacting tool.

7. A prosthetic device comprising:
   a liner comprising:
      an articulating surface configured to receive an opposing articular component; and
   a rim, wherein the articulating surface includes at least one constraining extension that extends above the rim, the at least one constraining extension having an extension articulating surface and an outer surface;
      a shroud having a hub configured to frictionally engage the extension articulating surface, wherein the shroud includes an outer rim that defines an opening, the hub is seated in the shroud opening, and the at least one constraining extension is disposed in the opening between the hub and the rim; and
      a guard configured to frictionally engage the outer surface of the at least one constraining extension.

8. The device of claim 7, wherein the shroud further includes a plurality of bridge members radially spaced about the hub.

9. The device of claim 7, wherein the hub has a concave impaction surface configured to receive a convex impaction tool.

10. The device of claim 7, wherein the hub includes an aperture that extends entirely through the hub.

11. The device of claim 7, further comprising a shell having a shell rim, the shell sized to receive the liner.

12. The device of claim 11, wherein the liner rim includes a flange configured to seat on at least a portion of the shell rim.

13. The device of claim 7, wherein at least a portion of the shroud is constructed of a metal.

* * * * *